(12) United States Patent
O'Brien et al.

(10) Patent No.: US 11,559,278 B2
(45) Date of Patent: *Jan. 24, 2023

(54) SYSTEMS AND METHODS FOR VASCULAR MAPPING

(71) Applicant: NovaSignal Corp., Los Angeles, CA (US)

(72) Inventors: Michael O'Brien, Los Angeles, CA (US); Mina Ranjbaran, Los Angeles, CA (US); Leo Petrossian, Los Angeles, CA (US); Robert Hamilton, Los Angeles, CA (US); Shankar Radhakrishnan, Los Angeles, CA (US); Corey M. Thibeault, Los Angeles, CA (US); Samuel G. Thorpe, Los Angeles, CA (US); Nicolas Canac, Los Angeles, CA (US)

(73) Assignee: NovaSignal Corp., Los Angeles, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/508,867

(22) Filed: Oct. 22, 2021

(65) Prior Publication Data

US 2022/0039775 A1 Feb. 10, 2022

Related U.S. Application Data

(63) Continuation of application No. 16/246,419, filed on Jan. 11, 2019, now Pat. No. 11,154,273.

(Continued)

(51) Int. Cl.
*A61B 8/00* (2006.01)
*A61B 8/06* (2006.01)
(Continued)

(52) U.S. Cl.
CPC ............. *A61B 8/4218* (2013.01); *A61B 8/06* (2013.01); *A61B 8/0808* (2013.01);
(Continued)

(58) Field of Classification Search
CPC ........... A61B 8/00; A61B 8/08; A61B 8/0808; A61B 8/0816; A61B 8/0891;
(Continued)

(56) References Cited

U.S. PATENT DOCUMENTS

| 5,379,770 A | 1/1995 | Van Veen |
|---|---|---|
| 6,196,972 B1 | 3/2001 | Moehring |

(Continued)

OTHER PUBLICATIONS

Final Office Action dated Dec. 30, 2020, from U.S. Appl. No. 16/246,419.

(Continued)

*Primary Examiner* — Carolyn A Pehlke
(74) *Attorney, Agent, or Firm* — Foley & Lardner LLP

(57) ABSTRACT

Systems, apparatuses, methods, and non-transitory computer-readable media for mapping a section of a vasculature of a subject are described herein, including moving a probe to a first position at a body of the subject adjacent the section of the vasculature; transmitting, by the probe, a first ultrasound beam into a first portion of the section of the vasculature through the body of the subject; receiving first ultrasound data including at least one imaging parameter of the first portion based on the first ultrasound beam; moving the probe to a second position at the body of the subject adjacent the section of the vasculature and different from the first position; transmitting, by the probe, a second ultrasound beam into a second portion of the section of the vasculature through the body of the subject; receiving second ultrasound data including the at least one imaging parameter of the second portion based on the second ultrasound beam; and (Continued)

constructing a map of the section of the vasculature based on the first ultrasound data and the second ultrasound data.

18 Claims, 7 Drawing Sheets

Related U.S. Application Data

(60) Provisional application No. 62/655,121, filed on Apr. 9, 2018, provisional application No. 62/616,419, filed on Jan. 11, 2018.

(51) Int. Cl.
    *A61B 8/08*         (2006.01)
    *A61B 34/30*       (2016.01)
    *A61B 5/00*         (2006.01)

(52) U.S. Cl.
    CPC .......... *A61B 8/0891* (2013.01); *A61B 8/4245* (2013.01); *A61B 8/4444* (2013.01); *A61B 8/483* (2013.01); *A61B 8/486* (2013.01); *A61B 8/488* (2013.01); *A61B 8/5253* (2013.01); *A61B 5/4064* (2013.01); *A61B 8/429* (2013.01); *A61B 8/4483* (2013.01); *A61B 8/5207* (2013.01); *A61B 8/5246* (2013.01); *A61B 8/5292* (2013.01); *A61B 34/30* (2016.02)

(58) Field of Classification Search
    CPC ... A61B 8/4218; A61B 8/4209; A61B 8/4245; A61B 8/483; A61B 8/488; A61B 8/5207; A61B 8/5215; A61B 8/5246; A61B 5/4064; G06T 7/0012
    See application file for complete search history.

(56) References Cited

U.S. PATENT DOCUMENTS

| | | |
|---|---|---|
| 6,635,017 B1 | 10/2003 | Moehring et al. |
| 10,616,473 B2 | 4/2020 | Costa et al. |
| 11,090,026 B2 | 8/2021 | Hamilton et al. |
| 2010/0130866 A1 | 5/2010 | Main et al. |
| 2010/0249597 A1 | 9/2010 | Shi |
| 2016/0157826 A1 | 6/2016 | Sisodia et al. |
| 2016/0367217 A1 | 12/2016 | Flores et al. |
| 2017/0119347 A1 | 5/2017 | Flores et al. |
| 2017/0128036 A1 | 5/2017 | Tanter et al. |

OTHER PUBLICATIONS

Final Office Action dated Oct. 18, 2019, from U.S. Appl. No. 16/246,419.
International Preliminary Report on Patentability dated Jul. 23, 2020, from application No. PCT/US2019/013347.
International Search Report and Written Opinion dated Apr. 25, 2019, from application No. PCT/US2019/013347.
Lynden, et al., "Visualization of the Cerebral Circulation Using Three-dimensional Transcranial Power Doppler Ultrasound Imaging," Journal of Neuroimaging, Jan. 1997, vol. 7, No. 1, pp. 35-39.
Nicolaides, et al., Doppler Ultrasound Principles and Practice, https://sonoworld.com/client/fetus/html/doppler/capitulos-html/chapter_01.htm# intro, 2002.
Non-Final Office Action dated Jul. 2, 2019, from U.S. Appl. No. 16/246,419.
Non-Final Office Action dated Mar. 18, 2020, from U.S. Appl. No. 16/246,419.
Notice of Allowance dated Jun. 21, 2021, from U.S. Appl. No. 16/246,419.
Australian Examination Report dated Nov. 22, 2022, from application No. 2019208041.

SYSTEMS AND METHODS FOR VASCULAR MAPPING

CROSS-REFERENCE TO RELATED PATENT APPLICATIONS

The present disclosure claims priority to, and the benefit of, U.S. provisional patent application Ser. No. 62/616,419, titled MAPPING OF CEREBRAL VASCULATURE USING ULTRASOUND, and filed on Jan. 11, 2018, which is incorporated herein by reference in its entirety. The present disclosure further claims priority to, and the benefit of, U.S. provisional patent application Ser. No. 62/655,121, titled SYSTEMS AND METHODS FOR VASCULATURE MAPPING, and filed on Apr. 9, 2018, which is incorporated herein by reference in its entirety.

BACKGROUND

Ultrasound energy (e.g., pulse wave ultrasound) can be utilized to insonate a range of depths to represent velocity and intensity of flow over that particular range. For example, motion mode or multi-mode (M-Mode) energy (e.g., power or velocity M-Mode) of ultrasound has been developed to address difficulties in locating acoustic windows and blood flow in vessels. Furthermore, a robotic setup that controls multiple degrees of freedom (DOF) positioning of an ultrasound probe has been developed to automatically and precisely control insonation of a subject's vasculature.

SUMMARY

According to various arrangements, there is provided a method for mapping a section of a vasculature of a subject. The method includes moving a probe to a first position at a body of the subject adjacent the section of the vasculature. The method further includes transmitting, by the probe, a first ultrasound beam into a first portion of the section of the vasculature through the body of the subject. The method further includes receiving first ultrasound data including at least one imaging parameter of the first portion based on the first ultrasound beam. The method further includes moving the probe to a second position at the body of the subject adjacent the section of the vasculature and different from the first position. The method further includes transmitting, by the probe, a second ultrasound beam into a second portion of the section of the vasculature through the body of the subject. The method further includes receiving second ultrasound data including the at least one imaging parameter of the second portion based on the second ultrasound beam. The method further includes constructing a map of the section of the vasculature based on the first ultrasound data and the second ultrasound data.

In some arrangements, the first position at the body of the subject is adjacent the head of the subject.

In some arrangements, the section of the vasculature includes the circle of Willis of the subject.

In some arrangements, the at least one imaging parameter includes presence and vector direction of blood flow.

In some arrangements, the vector direction indicates intensity of the blood flow away or towards the probe.

In some arrangements, the first position includes a first location along the body of the subject and a first orientation of the probe; the second position includes a second location along the body of the subject and a second orientation of the probe; and at least one of the first location is different from the second location or the first orientation is different from the second orientation.

In some arrangements, the first and second portions of the section of the vasculature are the same and the first and second ultrasound beams insonate the first and second portions at different angles.

In some arrangements, the first and second portions of the section of the vasculature are different.

In some arrangements, the first and second portions of the section of the vasculature overlap each other.

In some arrangements, the first and second ultrasound beams include a predetermined length.

In some arrangements, the predetermined length is about 60 millimeters.

In some arrangements, the first and second ultrasound data include the at least one imaging parameter at a plurality of different insonated depths along the first and second ultrasound beams, respectively.

In some arrangements, the plurality of insonated depths correspond to depths along the first and second ultrasound beams that overlap with the first and second portions of the section of the vasculature, respectively.

In some arrangements, constructing the map of the section of the vasculature includes generating coordinates of the first and second portions of the section of the vasculature in three-dimensional space.

In some arrangements, the coordinates of the first and second portions of the section of the vasculature are based on a plurality of insonated depths where the first and second ultrasound beams overlap the first and second portions.

In some arrangements, constructing the map of the section of the vasculature further includes connecting the coordinates of the first and second portions of the section of the vasculature in three-dimensional space.

In some arrangements, the first and second ultrasound beams include transcranial Doppler ultrasound.

In some arrangements, the probe is configured to move in at least two degrees of freedom (DOF).

According to various arrangements, a tool for mapping a section of a vasculature of a subject is provided. The tool includes a probe and a processing circuit. The processing circuit is configured to move the probe to a first position at a body of the subject adjacent the section of the vasculature. The probe is further configured to transmit, by the probe, a first ultrasound beam into a first portion of the section of the vasculature through the body of the subject. The probe is further configured to receive first ultrasound data including at least one imaging parameter of the first portion based on the first ultrasound beam. The probe is further configured to move the probe to a second position at the body of the subject adjacent the section of the vasculature and different from the first position. The probe is further configured to transmit, by the probe, a second ultrasound beam into a second portion of the section of the vasculature through the body of the subject. The probe is further configured to receive second ultrasound data including the at least one imaging parameter of the second portion based on the second ultrasound beam. The probe is further configured to construct a map of the section of the vasculature based on the first ultrasound data and the second ultrasound data.

According to various arrangements, there is provided a non-transitory computer-readable medium having computer-readable instructions such that, when executed by a processor, maps a section of a vasculature of a subject by moving a probe to a first position at a body of the subject adjacent the section of the vasculature; transmitting, by the probe, a first ultrasound beam into a first portion of the section of the vasculature through the body of the subject; receiving first ultrasound data including at least one imaging parameter of the first portion based on the first ultrasound beam; moving the probe to a second position at the body of the subject adjacent the section of the vasculature and different from the first position; transmitting, by the probe, a second ultrasound beam into a second portion of the section of the vasculature through the body of the subject; receiving second ultrasound data including the at least one imaging parameter of the second portion based on the second ultrasound beam; and constructing a map of the section of the vasculature based on the first ultrasound data and the second ultrasound data.

BRIEF DESCRIPTION OF THE FIGURES

Features and aspects of the present disclosure will become apparent from the following description and the accompanying example arrangements shown in the drawings, which are briefly described below.

DETAILED DESCRIPTION

Figure 1:
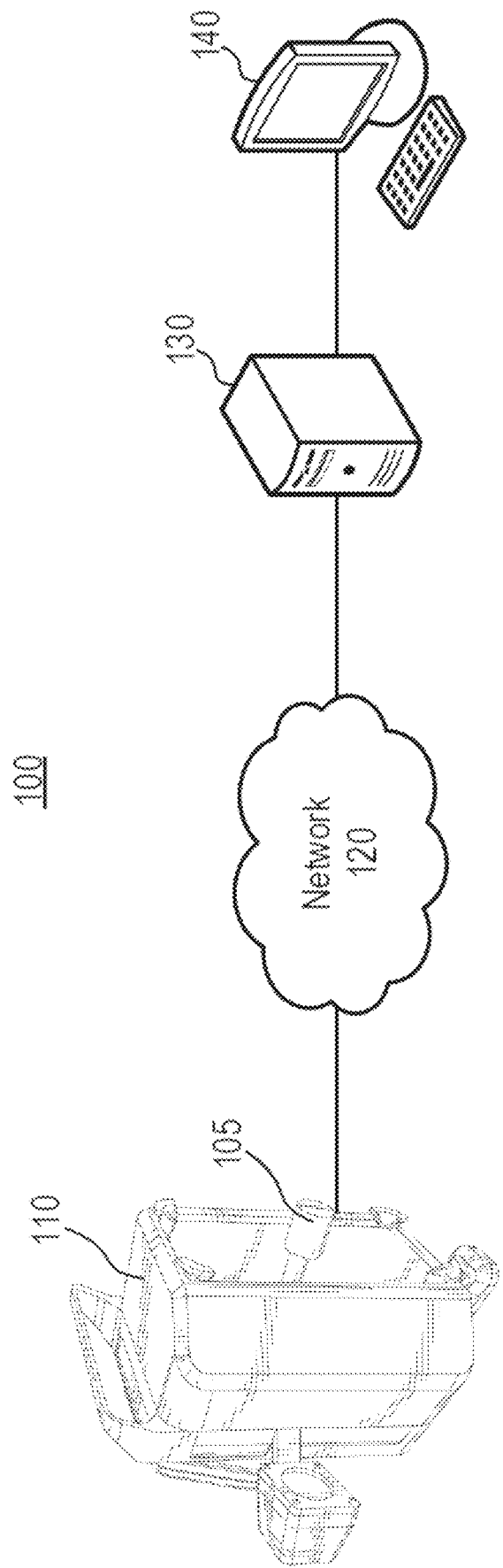
FIG. 1 is a schematic diagram illustrating a system for vascular mapping according to various arrangements.

The detailed description set forth below in connection with the appended drawings is intended as a description of various configurations and is not intended to represent the only configurations in which the concepts described herein may be practiced. The detailed description includes specific details for providing a thorough understanding of various concepts. However, it will be apparent to those skilled in the art that these concepts may be practiced without these specific details. In some instances, well-known structures and components are shown in block diagram form in order to avoid obscuring such concepts.

In the following description of various arrangements, reference is made to the accompanying drawings which form a part hereof and in which are shown, by way of illustration, specific arrangements in which the arrangements may be practiced. It is to be understood that other arrangements may be utilized, and structural changes may be made without departing from the scope of the various arrangements disclosed in the present disclosure.

According to various arrangements, there are provided systems and methods for vascular mapping utilizing ultrasound energy capable of obtaining blood flow information across multiple depths and a robotic apparatus capable of finely spanning the vasculature with the three-dimensional ultrasound beam profile to construct a three-dimensional representation of a subject's insonated vasculature. Currently, duplex systems are used to acquire a visualization (two-dimensional or three-dimensional) of vasculature in imaging modes (e.g., B-mode and C-mode) to be used in conjunction with pulse wave Doppler. Typically, the duplex system is costly and does not provide adequate resolution to provide certain blood flow information (e.g., velocity and is used in addition to a non-duplex ultrasound system (e.g., TCD). According to various arrangements, because mapping and visualization of vasculature can be performed in non-duplex systems (e.g., TCD systems that provide sufficient resolution of blood flow information), a costly separate duplex system is not required for vasculature mapping and would therefore simplify and make more efficient the healthcare process (with the capability to perform all the functions, including vascular mapping or visualization, at the single non-duplex ultrasound system) and save costs for healthcare providers while providing adequate resolution of desired information relating to blood flow (e.g., velocity).

In some arrangements, measuring ultrasound data in M-Mode provides signal velocity or power information at every depth of an anatomic feature (e.g., a brain) of a subject, between a minimum and maximum depth value. Typically, vessel insonation is improved when the probe is lined up parallel to the vessel (e.g., such that a length of the probe, and therefore an ultrasound beam emitted from the probe, is oriented along the same direction as the length of a vessel, and therefore the flow of blood within the vessel). Vessel insonation refers to ultrasound penetration of blood vessels. For a particular insonation target point (e.g., a particular anatomic feature of interest, such as a particular vessel or a particular point in the brain), vessel insonation can be optimized using the widest M-Mode band.

Further disclosure regarding M-Mode that can be utilized in conjunction with arrangements described herein can be found in U.S. Pat. No. 6,196,972, titled DOPPLER ULTRASOUND METHOD AND APPARATUS FOR MONITORING BLOOD FLOW, and filed on Nov. 11, 1998, which is incorporated herein by reference in its entirety.

FIG. 1 is a schematic diagram illustrating a system 100 according to various arrangements. Referring to FIG. 1, the system 100 includes at least a device 110, a controller 130, and an output device 140.

In some examples, the device 110 is an ultrasound device (e.g., imaging ultrasound or a TCD ultrasound device) configured to transmit and/or receive acoustic energy with respect to a subject (e.g., a head of the subject or other body part of the subject). The device 110 includes at least one transducer or probe 105 (e.g., at least one ultrasound probe) configured to transmit and/or receive ultrasound acoustic energy with respect to the subject. For example, the probe 105 includes at least one TCD transducer. The probe 105 can be configured to collect the ultrasound data in the manner described to find a high-quality signal within an acoustic window (e.g., temporal acoustic window). In some arrangements, an acoustic window is a location along the body of the subject that allows acoustic energy to pass therethrough (e.g., such that bone or other internal or external body part minimally interfere with the acoustic energy signal transmitted or received by the probe 105, for example, ultrasound energy signal). In other arrangements, the probe 105 can be configured to collect the ultrasound data in the manner described to find a high-quality signal within different acoustic windows such as but not limited to, a temporal window, a transorbital window, a suboccipital window, and so on. In some arrangements, the probe 105 is configured to collect ultrasound data from other parts of the body, such as, but not limited to, the neck, the internal carotid artery, chest, abdomen, legs, and so on. In particular arrangements, the probe 105 is configured to collect ultrasound data from any portion of a subject's body that provides access to a section of vasculature. In some arrangements, the system 100 includes two devices 110, each device 110 including an ultrasound probe 105, which can be placed near or on the body in locations, such as, but not limited to, the temporal window region on either side of the head (e.g., a first device 110 including a probe 105 at a first side of the head and a second device 110 including a probe 106 at a second side of the head that is opposite to the first side of the head). An acoustic coupling gel can be applied between the head and the probe 105 to improve acoustic transmission or reception.

The controller 130 is configured to receive the ultrasound data collected and output by the device 110 and to perform signal processing for the ultrasound data (e.g., construction of a representation of the subject's vasculature based on the ultrasound data). In that regard, the device 110 is operatively coupled to the controller 130 via a suitable network 120 to send the ultrasound data to the controller 130. The network 120 can be wired or wireless (e.g., 802.11X, ZigBee, Bluetooth®, Wi-Fi, or the like). The controller 130 is configured to assess signal quality of the ultrasound data in the manner described. In some examples, the controller 130 is further configured to perform signal processing functions such as but not limited to, beat segmentation, morphological feature identification, digital signal processing, and so on to facilitate a physician, clinician, technician, or healthcare provider with diagnosis. In some arrangements, the controller 130, the output device 140, and a portion of the network 120 are incorporated into a single device (e.g., a touchscreen tablet device).

In some arrangements, the output device 140 includes any suitable device configured to display information, results, messages, and the like to an operator (e.g., a physician, clinician, technician, or care provider) of the system 100. For example, the output device 140 includes but is not limited to, a monitor, a touchscreen, audio speaker, or any other output device configured to display the ultrasound data (e.g., cerebral blood flow velocity (CBFV) waveforms, M-Mode data, spectral data), morphology indicators corresponding to the ultrasound data, visualization of mapping of the subject's vasculature, and so on for facilitating diagnosis.

In some arrangements, the system 100 as described herein is used in conjunction with or for other diagnostic ultrasound procedures, such as, but not limited to, needle guidance, intravascular ultrasound (e.g., examination of vessels, blood flow characteristics, clot identification, emboli monitoring, and so on), echocardiograms, abdominal sonography (e.g., imaging of the pancreas, aorta, inferior vena cava, liver, gall bladder, bile ducts, kidneys, spleen, appendix, rectal area, and so on), gynecologic ultrasonography (e.g., examination of pelvic organs such as uterus, ovaries, Fallopian tubes, and so on), obstetrical sonography, otolaryngological sonography (e.g., imaging of the thyroid (such as for tumors and lesions), lymph nodes, salivary glands, and so on), neonatal sonography (e.g., assessment of intracerebral structural abnormalities through soft spots of a skull of an infant, bleeds, ventriculomegaly, hyrdrocephalus, anoxic insults, and so on), ophthamological procedures (e.g., A-scan ultrasound biometry, B-scan ultrasonography, and so on), pulmonological uses (e.g., endobronchial ultrasound (EBUS)), urological procedures (e.g., determination of an amount of fluid retained in a subject's bladder, imaging of pelvic organs (such as uterus, ovaries, urinary bladder, prostate, and testicles), and detection of kidney stones), scrotal sonography (e.g., to evaluate testicular pain, identify solid masses, and so on), musculoskeletal procedures (e.g., examination of tendons, muscles, nerves, ligaments, soft tissue masses, bone surfaces, and so on), bone fracture sonography, testing for myopathic disease, estimating lean body mass, proxy measures of muscle quality (e.g., tissue composition), nephrological procedures (e.g., renal ultrasonography), and the like.

In some arrangements, the system 100 as described herein is used in conjunction with therapeutic ultrasound procedures, such as, but not limited to, high-intensity focused ultrasound (HIFU), focused ultrasound surgery (FUS), Magnetic resonance-guided focused ultrasound (MRgFUS), lithotripsy (e.g., breaking up kidney stones, bezoars, gall stones, and the like), targeted ultrasound drug delivery, trans-dermal ultrasound drug delivery, ultrasound hemostasis, cancer therapy, ultrasound-assisted thrombolysis, dental hygiene (e.g., cleaning teeth), phacoemulsification, ablation (e.g., of tumors or other tissue), acoustic targeted drug delivery (ATDD), trigger release of drugs (e.g., anti-cancer drugs), ultrasound-guided treatments (sclerotherapy, endovenous laser treatment, liposuction, and so on), and the like. In some arrangements, ultrasound is used for physical therapy applications, including, but not limited to, stimulating tissue beneath the skin's surface (e.g., by using very high frequency sound waves, such as, as an example, between about 800,000 Hz and 2,000,000 Hz), treating musculoskeletal ailments with ultrasound exposure (e.g., ligament sprains, muscle strains, tendonitis, joint inflammation, plantar fasciitis, metatarsalgia, facet irritation, impingement syndrome, bursitis, rheumatoid arthritis, osteoarthritis, and scar tissue adhesion), and the like.

Figure 2:
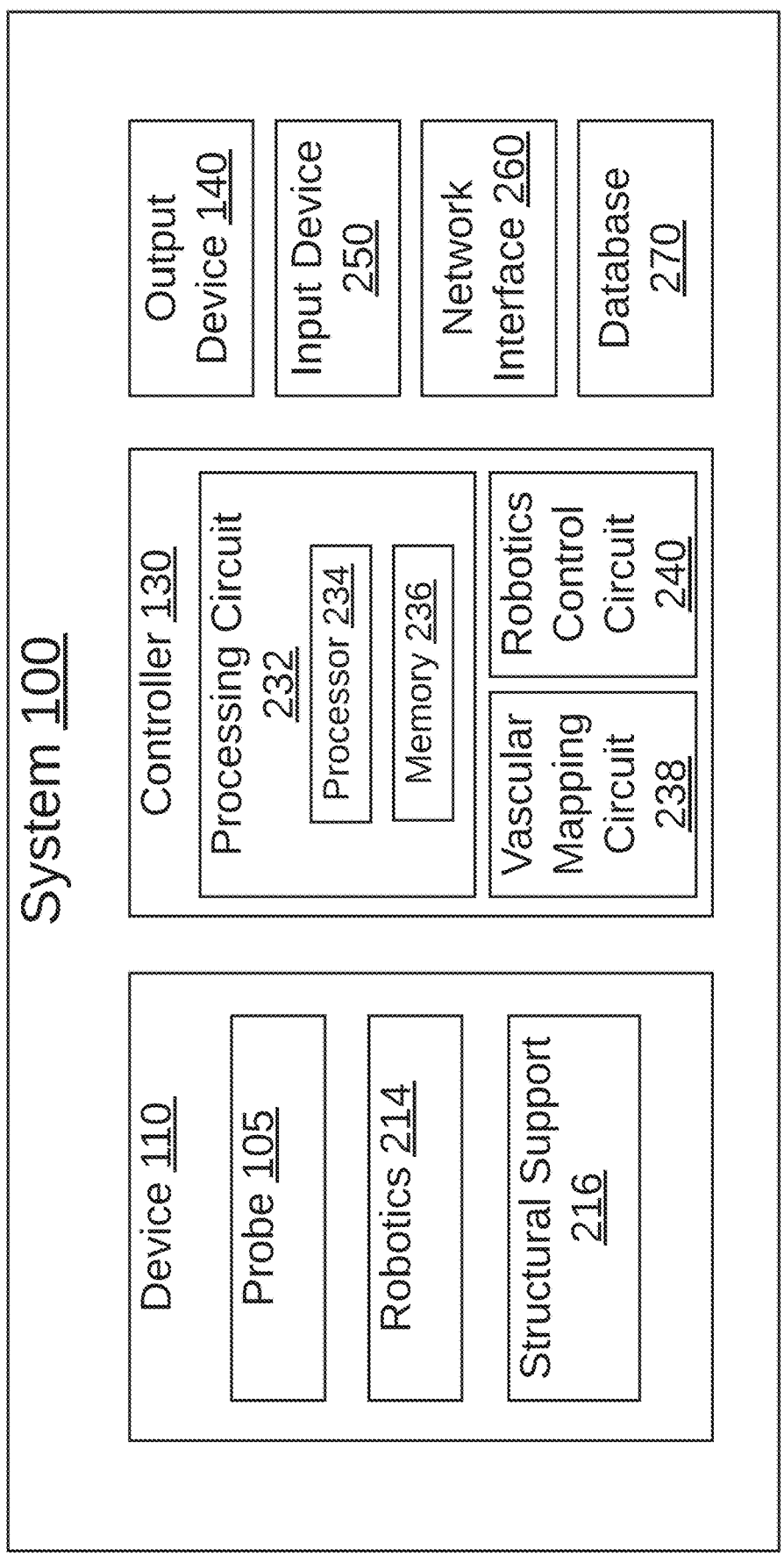
FIG. 2 is a schematic block diagram illustrating the system shown in FIG. 1 according to various arrangements.

FIG. 2 is a schematic block diagram illustrating the system 100 shown in FIG. 1 according to various arrangements. Referring to FIGS. 1-2, the device 110 includes the probe 105 as described. Further disclosure regarding examples of the probe 105 that can be used in conjunction with the system 100 described herein can be found in non-provisional publication no. US 2017-0119347 A1, titled ROBOTIC SYSTEMS FOR CONTROL OF AN ULTRASONIC PROBE, and filed on Jan. 5, 2017, which is incorporated herein by reference in its entirety. In some arrangements, the device 110 is configured to automatically or robotically operate the probe 105.

In some arrangements, the device 110 includes robotics 214 configured to control positioning of the probe 105. For example, the robotics 214 are configured to translate the probe 105 along a surface of the body of the subject (e.g., the subject's head) and to move the probe 105 with respect to (e.g., toward and away from) the subject's body along various axes in the Cartesian, spherical, and rotational coordinate systems. In particular, the robotics 214 can include a multiple degree of freedom (DOF) TCD transducer positioning system with motion planning. In some arrangements, the robotics 214 are capable of supporting one, two, three, four, five, or six DOF movements of the probe 105 with respect to the subject's body. In some instances, the robotics 214 can translate in X and Y axes (e.g., along a surface of the head) to locate a temporal window region in translational axes, and in Z axis with both force and position feedback control to both position and maintain the appropriate force against the skull/skin to maximize signal quality by maintaining appropriate contact force. Two angular DOF (e.g., pan and tilt) may be used to maximize normal insonation of blood vessels to maximize velocity signals.

In some arrangements, an end of the probe 105 is operatively coupled to or otherwise interfaces with the robotics 214. The robotics 214 include components, such as but not limited to a motor assembly and the like for controlling the positioning of the probe 105 (e.g., controlling z-axis pressure, normal alignment, or the like of the probe 105). In some arrangements, the registration of the probe 105 against the head 105 is accomplished using the robotics 214 to properly position and align the probe 105 in the manner described.

In some arrangements, the probe 105 includes a first end and a second end that is opposite to the first end. In some arrangements, the first end includes a concave surface that is configured to be adjacent to or contact a scanning surface on the head. The concave surface is configured with a particular pitch to focus generated energy towards the scanning surface. In some arrangements, the device 110 is a TCD apparatus such that the first end of the probe 105 is configured to be adjacent to or contact and align along a side of the head. The first end of the probe 105 is configured to provide ultrasound wave emissions from the first end and directed into the head (e.g., toward the brain). For example, the first end of the probe 105 can include a transducer (such as, but not limited to, an ultrasound transducer, TCD, transcranial color-coded sonography (TCCS), or acoustic ultrasound transducer array such as sequential arrays or phased arrays) that emits acoustic energy capable of penetrating windows in the skull/head or neck.

In some arrangements, the second end of the probe 105 is coupled to the robotics 214. In some arrangements, the second end of the probe 105 includes a threaded section along a portion of the body of the probe 105. The second end is configured to be secured in the robotics 214 via the threads (e.g., by being screwed into the robotics 214). In other arrangements, the probe 105 is secured in the robotics 214 by any other suitable connecting means, such as but not limited to welding, adhesive, one or more hooks and latches, one or more separate screws, press fittings, or the like.

The device 110 can further include a structural support 216 configured to support the head of the subject and/or to support the device 110 on the head or other parts of the body of the subject. In some examples, the structural support 216 includes a platform (e.g., a baseplate) that allows the subject to lay down on a flat surface in a reclined or supine position while the device 110 is operational. The structural support 216 can be made from any suitably malleable material that allows for flexing, such as, but not limited to, flexible plastics, polyethylene, urethanes, polypropylene, ABS, nylon, fiber-reinforced silicones, structural foams, or the like.

In some arrangements, the system 100 includes an input device 250. The input device 250 includes any suitable device configured to allow an operator, physician, or care provider personnel to input information or commands into the system 100. In some arrangements, the input device 250 includes but is not limited to, a keyboard, a keypad, a mouse, a joystick, a touchscreen display, a microphone, or any other input device performing a similar function. In some arrangements, the input device 250 and the output device 140 can be a same input/output device (e.g., a touchscreen display device).

In some arrangements, the network interface 260 is structured for sending and receiving data (e.g., results, instructions, requests, software or firmware updates, and the like) over a communication network (e.g., the network 120). Accordingly, the network interface 260 includes any of a cellular transceiver (for cellular standards), local wireless network transceiver (for 802.11X, ZigBee, Bluetooth®, Wi-Fi, or the like), wired network interface, a combination thereof (e.g., both a cellular transceiver and a Bluetooth transceiver), and/or the like. In some examples, the network interface 260 includes any method or device configured to send data from the device 110 to the controller 130. In that regard, the network interface 260 may include Universal Serial Bus (USB), FireWire, serial communication, and the like.

In some arrangements, the input device 250, the output device 140, the network interface 260, and the controller 130 form a single computing system that resides on a same node on the network 120. The device 110 is configured to be connected to the computing system via the network 120. The network interface 260 is configured to communicate data to and from the device 110 via the network 120. In such arrangements, the device 110 includes a similar network interface (not shown) to communicate data to and from the computing device via the network 120. In other arrangements in which the device 110, the controller 130, the output device 140, the input device 250, and the network interface 260 all reside in a same computing device on a same node of a network, the network interface 260 is configured to communicate data with another suitable computing system (e.g., cloud data storage, remote server, and the like).

In some arrangements, the controller 130 is configured for controlling operations, processing data, executing input commands, providing results, and so on. For example, the controller 130 is configured to receive input data or instructions from the input device 250 or the network interface 260, to control the system 100 to execute the commands, to receive data from the device 110, to provide information to the output device 140 or network interface 260, and so on.

The controller 130 includes a processing circuit 232 having a processor 234 and a memory 236. In some arrangements, the processor 234 can be implemented as a general-purpose processor and is coupled to the memory 236. The processor 234 includes any suitable data processing device, such as a microprocessor. In the alternative, the processor 234 includes any suitable electronic processor, controller, microcontroller, or state machine. In some arrangements, the processor 234 is implemented as a combination of computing devices (e.g., a combination of a Digital Signal Processor (DSP) and a microprocessor, a plurality of microprocessors, at least one microprocessor in conjunction with a DSP core, or any other such configuration). In some arrangements, the processor 234 is implemented as an Application Specific Integrated Circuit (ASIC), one or more Field Programmable Gate Arrays (FPGAs), a Digital Signal Processor (DSP), a group of processing components, or other suitable electronic processing components.

In some arrangements, the memory 236 includes a non-transitory processor-readable storage medium that stores processor-executable instructions. In some arrangements, the memory 236 includes any suitable internal or external device for storing software and data. Examples of the memory 236 include but are not limited to, Random Access Memory (RAM), Read-Only Memory (ROM), Non-Volatile RAM (NVRAM), flash memory, floppy disks, hard disks, dongles or other Recomp Sensor Board (RSB)-connected memory devices, or the like. The memory 236 can store an Operating System (OS), user application software, and/or executable instructions. The memory 236 can also store application data, such as an array data structure. In some arrangements, the memory 236 stores data and/or computer code for facilitating the various processes described herein.

As used herein, the term "circuit" can include hardware structured to execute the functions described herein. In some arrangements, each respective circuit can include machine-readable media for configuring the hardware to execute the functions described herein. The circuit can be embodied as one or more circuitry components including, but not limited to, processing circuitry, network interfaces, peripheral devices, input devices, output devices, sensors, etc. In some arrangements, a circuit can take the form of one or more analog circuits, electronic circuits (e.g., integrated circuits (IC), discrete circuits, system on a chip (SOCs) circuits, etc.), telecommunication circuits, hybrid circuits, and any other suitable type of circuit. In this regard, the circuit can include any type of component for accomplishing or facilitating achievement of the operations described herein. For example, a circuit as described herein can include one or more transistors, logic gates (e.g., NAND, AND, NOR, OR, XOR, NOT, XNOR, etc.), resistors, multiplexers, registers, capacitors, inductors, diodes, wiring, and so on.

The circuit can also include one or more processors communicatively coupled to one or more memory or memory devices. In this regard, the one or more processors can execute instructions stored in the memory or can execute instructions otherwise accessible to the one or more processors. In some arrangements, the one or more processors can be embodied in various ways. The one or more processors can be constructed in a manner sufficient to perform at least the operations described herein. In some arrangements, the one or more processors can be shared by multiple circuits (e.g., a first circuit and a second circuit can comprise or otherwise share the same processor which, in some example arrangements, can execute instructions stored, or otherwise accessed, via different areas of memory). Alternatively, or additionally, the one or more processors can be structured to perform or otherwise execute certain operations independent of one or more co-processors. In other example arrangements, two or more processors can be coupled via a bus to enable independent, parallel, pipelined, or multi-threaded instruction execution. Each processor can be implemented as one or more general-purpose processors, ASICs, FPGAs, DSPs, or other suitable electronic data processing components structured to execute instructions provided by memory. The one or more processors can take the form of a single core processor, multi-core processor (e.g., a dual core processor, triple core processor, quad core processor, etc.), microprocessor, etc. In some arrangements, the one or more processors can be external to the apparatus, for example, the one or more processors can be a remote processor (e.g., a cloud-based processor). Alternatively, or additionally, the one or more processors can be internal and/or local to the apparatus. In this regard, a given circuit or components thereof can be disposed locally (e.g., as part of a local server, a local computing system, etc.) or remotely (e.g., as part of a remote server such as a cloud-based server). To that end, a circuit, as described herein can include components that are distributed across one or more locations.

An example system for implementing the overall system or portions of the arrangements can include a general-purpose computer, including a processing unit, a system memory, and a system bus that couples various system components including the system memory to the processing unit. Each memory device can include non-transient volatile storage media, non-volatile storage media, non-transitory storage media (e.g., one or more volatile and/or non-volatile memories), etc. In some arrangements, the non-volatile media may take the form of ROM, flash memory (e.g., flash memory such as NAND, 3D NAND, NOR, 3D NOR, etc.), Electrically Erasable Programmable Read-Only Memory (EEPROM), Magnetoresistive Random Access Memory (MRAM), magnetic storage, hard discs, optical discs, etc. In other arrangements, the volatile storage media can take the form of RAM, Thyristor Random Access Memory (TRAM), Z-Capacitor Random Access Memory (ZRAM), etc. Combinations of the above are also included within the scope of machine-readable media. In this regard, machine-executable instructions comprise, for example, instructions and data which cause a general-purpose computer, special purpose computer, or special purpose processing machines to perform a certain function or group of functions. Each respective memory device can be operable to maintain or otherwise store information relating to the operations performed by one or more associated circuits, including processor instructions and related data (e.g., database components, object code components, script components, etc.), in accordance with the example arrangements described herein.

The controller 130 further includes a vascular mapping circuit 238, which can be implemented with the processing circuit 232 or another dedicated processing circuit. In some examples, the vascular mapping circuit 238 can be implemented with two or more circuits. The vascular mapping circuit 238 is configured to control the probe 105 and other components of the system 100 (e.g., the controller 130) to perform various tasks associated with mapping a section of vasculature of a subject, including, transmitting the acoustic energy into the vasculature, collecting and aggregating acoustic data based on the transmitted energy, constructing a mapping of the section of the vasculature based on the collected acoustic data, and other tasks described herein.

The controller 130 further includes a robotics control circuit 240, which can be implemented with the processing circuit 232 or another dedicated processing circuit. The robotics control circuit 240 is configured to control the robotics 214 to move the probe 105 in the manner described herein.

Figure 3:
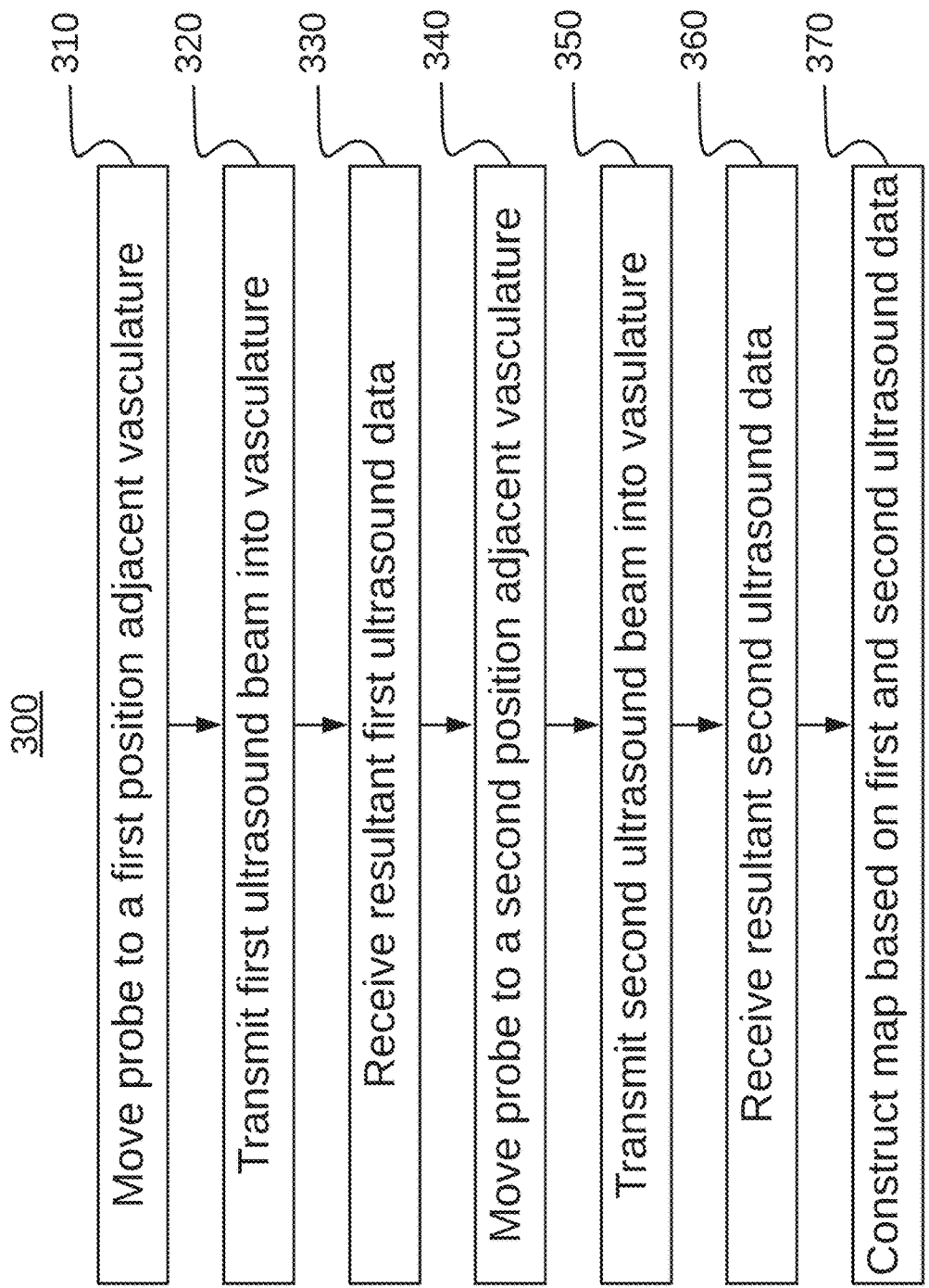
FIG. 3 is a process flow diagram illustrating a method for vascular mapping using the system shown in FIG. 1 according to various arrangements.

FIG. 3 is a process flow diagram illustrating a method 300 for vascular mapping using the system 100 according to various arrangements. Referring to FIGS. 1-3, at 310, the robotics 214 are configured by the robotics control circuit 240 to move the probe 105 to a first position on a subject. The probe 105 may be controlled to move within a workspace at the subject, as described with respect to FIG. 4A.

In some arrangements, a position of the probe 105 at a subject includes a location of the probe 105 at the subject and an orientation of the probe 105 with respect to the subject and at the location of the probe 105. Accordingly, the robotics control circuit 240 is configured to instruct the probe via the robotics 214 to move along the subject and rotate the probe 105 at various degrees of rotation to allow the probe 105, for example, five or more DOF. In particular arrangements, the robotics 214 that are controlled by the robotics control circuit 240 are configured to provide a five DOF automated robotic system that can be used, in conjunction with the probe 105 (e.g., an ultrasound probe, for example, a TCD probe), to locate an acoustic window (e.g., a transtemporal acoustic window) and measure blood flow characteristics of a section of vasculature in the subject using the probe 105. For example, the robotics 214 are configured to translate and rotate the probe 105 in an X-axis (e.g., laterally along the subject), Y-axis (e.g., laterally along the subject along an axis perpendicular to the X-axis), rotation in a direction along the X-axis, and rotation in a direction along the Y-axis, while keeping contact along a Z-axis (e.g., telescoping towards and away from the subject along an axis that is perpendicular to the X-axis and Y-axis) with the subject's acoustic window with a constant force.

In some arrangements, the robotics 214 are configured to allow fine increments in translation and rotation of the probe 105 to allow the probe 105 to provide a thorough spanning of a section of the vasculature within a subject using acoustic energy (e.g., ultrasound energy) emanated by the probe 105. For example, although the probe 105 can be moved by the robotics 214 to a particular location at the subject. Accordingly, in some arrangements, the system 100 is capable of mapping a section of a vasculature of a subject in three-dimensional space by finely moving the probe to various positions along a subject's acoustic window and emanating a beam of ultrasound energy after each movement to collect and aggregate ultrasound data from the individual ultrasound beams that insonate differing portions of the section of the vasculature (e.g., different portions or the same portion at different angles of insonation) that can then be used to construct the vasculature map, as further described below.

As such, in some arrangements, at step 310, the robotics 214 controlled by the robotics control circuit 240 are configured to move the probe 105 to the first position that includes a first location and a first orientation of the probe 105. The first location is along the subject (e.g., at an acoustic window of the subject) and is adjacent or proximate the section of vasculature that is to be insonated by the acoustic energy generated by the probe 105. For example, the probe 105 is external the body of the subject while the section of the vasculature is internal the body of the subject while the probe 105 and the section of the vasculature are adjacent or proximate to each other. The section of the vasculature to be insonated can include any section of vasculature in the subject that is desired to be mapped, such as, but not limited to the circle of Willis within the brain of the subject.

At 320, the probe 105 transmits a first ultrasound beam (e.g., as controlled by the vascular mapping circuit 238) into the section of vasculature that is to be mapped. In some arrangements, the first ultrasound beam includes an ultrasound beam configured to insonate the section of vasculature at multiple depths.

At 330, the vascular mapping circuit 238 receives first ultrasound data that is based on and results from the first ultrasound beam transmitted at step 320. In particular arrangements, because the first ultrasound beam is configured to insonate the section of the vasculature at multiple depths, the first ultrasound data includes information of the section of the vasculature at multiple insonated depth (assuming the first ultrasound beam overlaps with the section of the vasculature at the multiple depths). In other words, the first ultrasound data includes imaging information about the section of the vasculature at one or more portions of the section of the vasculature where the first ultrasound beam intersects with the section of the vasculature.

In some arrangements, the first ultrasound data includes information relating to an imaging parameter at the one or more insonated depths of the section of the vasculature. For example, the imaging parameter can include information relating to blood flow at the one or more insonated portions of the vasculature. In particular arrangements, the imaging parameter includes one or more of presence of blood flow, direction of blood flow, and intensity of blood flow at the one or more insonated portions of the section of the vasculature. For example, the imaging parameter can provide data pertaining to vector direction of blood flow, and so the direction and magnitude components of the vector direction can help with building up intensity-based vessel maps. In some arrangements, the first ultrasound data includes M-Mode ultrasound data, which is a result of processing the returning first ultrasound beam information at the multiple depths of the first ultrasound beam.

At 340, the robotics 214 are configured by the robotics control circuit 240 to move the probe 105 to a second position on a subject. Step 340 is similar to step 310 and therefore the description provided with respect to step 310 above is applicable to step 340. In some arrangements, the second position is different than the first position. For example, the probe 105 at the second position can have a second location along the body of the subject and a second orientation of the probe at the second location that are both different from the first location and the first orientation of the first position of the probe 105, respectively. As another example, the first location of the first position and the second location of the second position are the same, but the first orientation of the first position and the second orientation of the second position are different (e.g., the probe 105 remains at the same location at the body of the subject but at a different orientation with respect to the body of the subject). As yet another example, the first location of the first position and the second location of the second position are different, but the first orientation of the first position and the second orientation of the second position are the same (e.g., the probe 105 remains at the same orientation with respect to the body of the subject but at a different location along the body of the subject).

At 350, the probe 105 transmits a second ultrasound beam (e.g., as controlled by the vascular mapping circuit 238) into the section of vasculature that is to be mapped. The second ultrasound beam is transmitted while the probe is in the second position that is different from the first position such that the position of the second ultrasound beam at the section of the vasculature is different from that of the first ultrasound beam. In some arrangements, the second ultrasound beam also includes an ultrasound beam configured to insonate the section of vasculature at multiple depths.

At 360, the vascular mapping circuit 238 receives second ultrasound data that is based on and results from the second ultrasound beam transmitted at step 320. Step 360 is similar to step 330 and therefore the description provided with respect to step 330 above is applicable to step 360. In some arrangements, because the probe 105 is in the second position different from the first position the second ultrasound data reflects a different portion of the section of the vasculature than does the first ultrasound data. For example, because the robotics 214 are configured to move the probe 105 in fine increments, the first ultrasound data and the second ultrasound data include information regarding portions of the section of the vasculature that significantly overlap, but yet are still different in the portions of the section of the vasculature that are insonated. As another example, the first and second positions of the probe 105 can be far from each other or have a significant difference in orientation of the probe 105 such that the first ultrasound data and the second ultrasound data include information regarding portions of the section of the vasculature that do not significantly overlap or that are completely distinct.

At 370, the vascular mapping circuit 238 constructs a map of the section of the vasculature based on the first ultrasound data and the second ultrasound data. In some arrangements, the vascular mapping circuit 238 makes a determination as to whether enough ultrasound data has been acquired before initiating construction of the map. For example, the vascular mapping circuit 238 can track and base this determination on how many ultrasound insonations have occurred in a certain period of time, the amount of ultrasound data received, the number of movements of the probe 105, the amount of time that has lapsed since the start of the vascular mapping process, and so on.

In other arrangements, the vascular mapping circuit 238 adds or refines the vascular map as ultrasound data is received for continuous construction of the map (e.g., based on blood flow directional vector from the previous positions). For example, based on the previous information received by the ultrasound beam, the vascular mapping circuit 238 can guide the robotics control circuit 240 to control the probe 105 to move to the next position for insonation such that the insonation pattern or strategy or path can be more efficient in insonating at optimal angles and positions to find more portions of the section of the vasculature more quickly. As an example, the vascular mapping circuit 238 can use the detected blood flow direction received from the ultrasound beam to inform a next insonation point (e.g., because the direction and magnitude of the blood flow of an insonated portion of the vasculature is received by the vascular mapping circuit 238, it can be known where that particular insonated vessel extends by following the blood flow such that the robotics 214 can move the probe 105, as controlled by the robotics control circuit 240, to insonate the next location where the vessel likely extends). In some arrangements, this can be referred to as vessel walking.

Further disclosure regarding guiding the position of the probe 105 based on previous blood flow information (e.g., vessel walking) that can be used in conjunction with the system 100 described herein can be found in U.S. Pat. No. 11,090,026, titled SYSTEMS AND METHODS FOR DETERMINING CLINICAL INDICATIONS, granted on Aug. 17, 2021, which is incorporated herein by reference in its entirety.

In some arrangements, because the coordinates of the probe 105 within the robotic system and the depths starting from the probe 105 of the insonated portions of the section of the vasculature are known (e.g., from the predetermined parameters of the robotic system and from the received ultrasound data, respectively), the vascular mapping circuit 238 can construct the insonated portions of the section of the vasculature in three-dimensional space). In other words, in some arrangements, positional information of the probe 105 from the robotic system are aligned with the ultrasound data based on the depths of insonation of the ultrasound beams. In some arrangements, Euler rotation matrices are used with this known information, and so the corresponding projections of the insonated portions of the section of the vasculature in the three-dimensional robotic reference frame can be determined. Accordingly, the vascular mapping circuit 238 can provide a visualization of the obtained coordinates in three-dimensional space that reflects topology of sections of vasculature of a subject.

In some arrangements, the probe 105 is held and manually manipulated by a human operator. In order to determine the position and orientation of the probe so that the image reconstruction can take place, additional methods of locating the probe 105 in space could be used including: position sensor located within the probe which is either an absolute position sensor or a relative displacement sensor, linear, angular, or multi axis position sensors located within the probe, imaging of the probe using a camera and determining its position, simultaneous imaging of the probe 105 and anatomical features so that anatomical landmarks on the subject are known relative to the location of the probe 105, adding markers (e.g. fiducials) on the probe 105 such that imaging can interpret its location as the marker is moved through space, and accelerometers which sense parameters such as tilt, movement and speed. Based on the resolution of the measurement and the ability to reconstruct a map from multiple measurements of the same position in space, the knowledge of the location of the probe 105 in space can be reduced (e.g., five degrees of freedom including X, Y, Z, pan and tilt) to less because multiple measurements of the same location can be stitched together.

In some arrangements, instead of using the method 300 for vascular mapping, other parts of the body of the subject can be imaged and a resulting map can therefore be constructed utilizing similar steps. For example, the ultrasound beams can be used to insonate an internal organ at multiple positions of the probe 105 to map and image a visualization of the organ (or bone, tissue, etc.).

In some arrangements, the vascular mapping circuit 238, for example at step 330 and step 360, receives the ultrasound data from the probe 105 at certain times that are associated with certain locations and orientations (first and second positions) of the probe 105 at those times. As such, in some arrangements, a time stamp of ultrasound data is matched with a time stamp of the robotics 214 attached to the probe 105. After matching the time stamps, using the position of the probe 105 and given the direction and length of the ultrasound beam originating from the probe 105, coordinates of the ultrasound insonation can be determined. Hence, the position of multiple portions of the vasculature that are insonated by the ultrasound beam at different depths can be cataloged in space, and all or some of the vasculature can be reconstructed by continuously moving the probe 105, emanating an ultrasound beam, and storing positional information of any resulting insonated vasculature portions.

Accordingly, in some arrangements, based on known anatomy, different parts of the vasculature can be identifiable based on insonation depths, blood flow direction, and vessel curvature. Furthermore, vascular mapping can help with vessel identification and navigation to ensure that ultrasound measurements are in correct regions desired for diagnostics. In addition, for stroke, vascular mapping can identify where an occlusion resides (e.g., by identifying a portion of the vasculature that should exhibit blood flow, based on the mapping and known anatomy, demonstrate poor or nonexistent blood flow), helping with an expedient intervention.

Accordingly, power M-Mode can be used to re-construct brain vasculature in 3D space. This non-invasive tool enables 3D vascular mapping, allowing for insight into cerebrovascular health unlocked by the rTCD system. Such mapping can help with vessel identification to assure TCD measurements are in regions required for assessment or aid in the comparison of different vessels for a wide range of pathologies.

In some arrangements, the mapping of the vasculature as described herein can be displayed (e.g., at the output device 140) in various forms to provide healthcare providers with convenient and informative visualizations. For example, while performing traditional ultrasound scans (e.g., to acquire blood flow velocity waveforms at particular portions of the cerebral vasculature, for example, at the middle cerebral artery), the mapping of the vasculature can be displayed while the ultrasound scan is performed so that the healthcare professional can conveniently and readily see exactly where in the vasculature the ultrasound beam is currently being projected so that the healthcare professional can be guided or can quickly find the desired section of vasculature that is to be insonated. In some arrangements, the mapping of the vasculature is used in generating medical reports so that the viewer of the reports can readily see where in the vasculature the blood flow information is coming from.

In some arrangements, fusion imaging is accomplished with the help of the vascular mapping. For example, in some arrangements, fusion imaging for TCD and other imaging modalities (e.g. computed tomography angiography (CTA), magnetic resonance imaging (MRI), and so on) can be used to align real time search and vessel mapping with what has been found in these imaging modalities. In some arrangements, the system 100, and particularly the robotics 214 controlled by the robotics control circuit 240, rely on fiducials at the subject in space for maneuvering the probe 105. These fiducials provide the system 100, and particularly the robotics 214 controlled by the robotics control circuit 240, knowledge of where the person is and therefore where the probe 105 is with respect to the other imaging modalities (e.g., CTA and MRI). For example, the other imaging modalities can also be accomplished with fiducials at the same place as those used in connection with the system 100, allowing for co-registration of the different imaging modalities.

Further disclosure regarding fiducials and registration of the system 100 can be found in U.S. Pat. No. 10,616,473, titled SYSTEMS AND METHODS FOR REGISTERING HEADSET SYSTEM, granted on Apr. 7, 2020, which is incorporated herein by reference in its entirety.

Figure 4A:
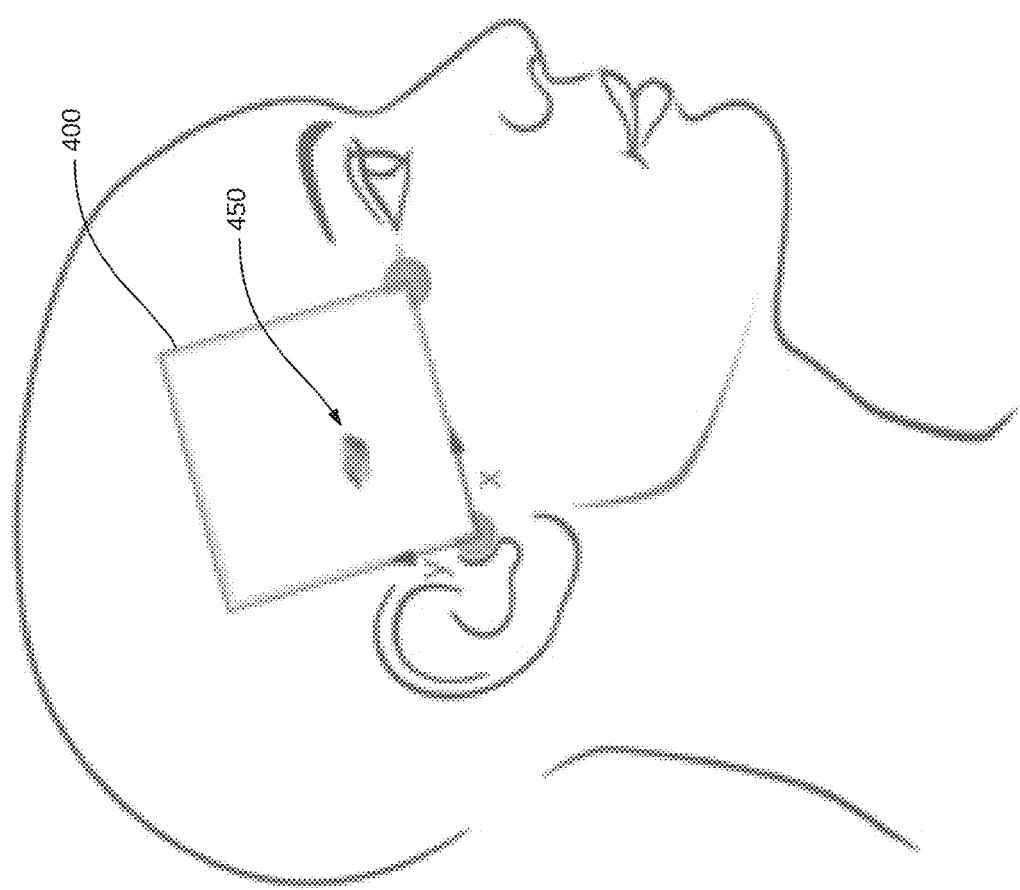
FIG. 4A is a schematic diagram illustrating an example workspace of a subject according to various arrangements.

FIG. 4A is a schematic diagram illustrating an example workspace 400 of a subject according to various arrangements.

Referring to FIGS. 1-4A, the workspace 400 of the probe 105 may correspond to a maximum allowable boundary which the robotics 214 can move the probe 105. While shown to be planar (e.g., in an XY-plane), the workspace 400 can be three-dimensional (in an XYZ-space). While the workspace 400 is shown to be square, the workspace 400 can have any suitable shape such as but not limited to, triangle, rectangle, circle, pentagon, hexagon, irregular shape, and so on.

In some arrangements, the workspace 400 corresponds to the subject's temporal acoustic window (e.g., the square between the subject's eye corner and tragus). As shown in FIG. 4, the workspace 400 is shown to have been scanned by the system 100 in the manner described herein at numerous positions 450 of the probe 105 (e.g., XY-coordinate locations along the subject's temporal region and at various angles of insonation of the probe 105).

Figure 4B:
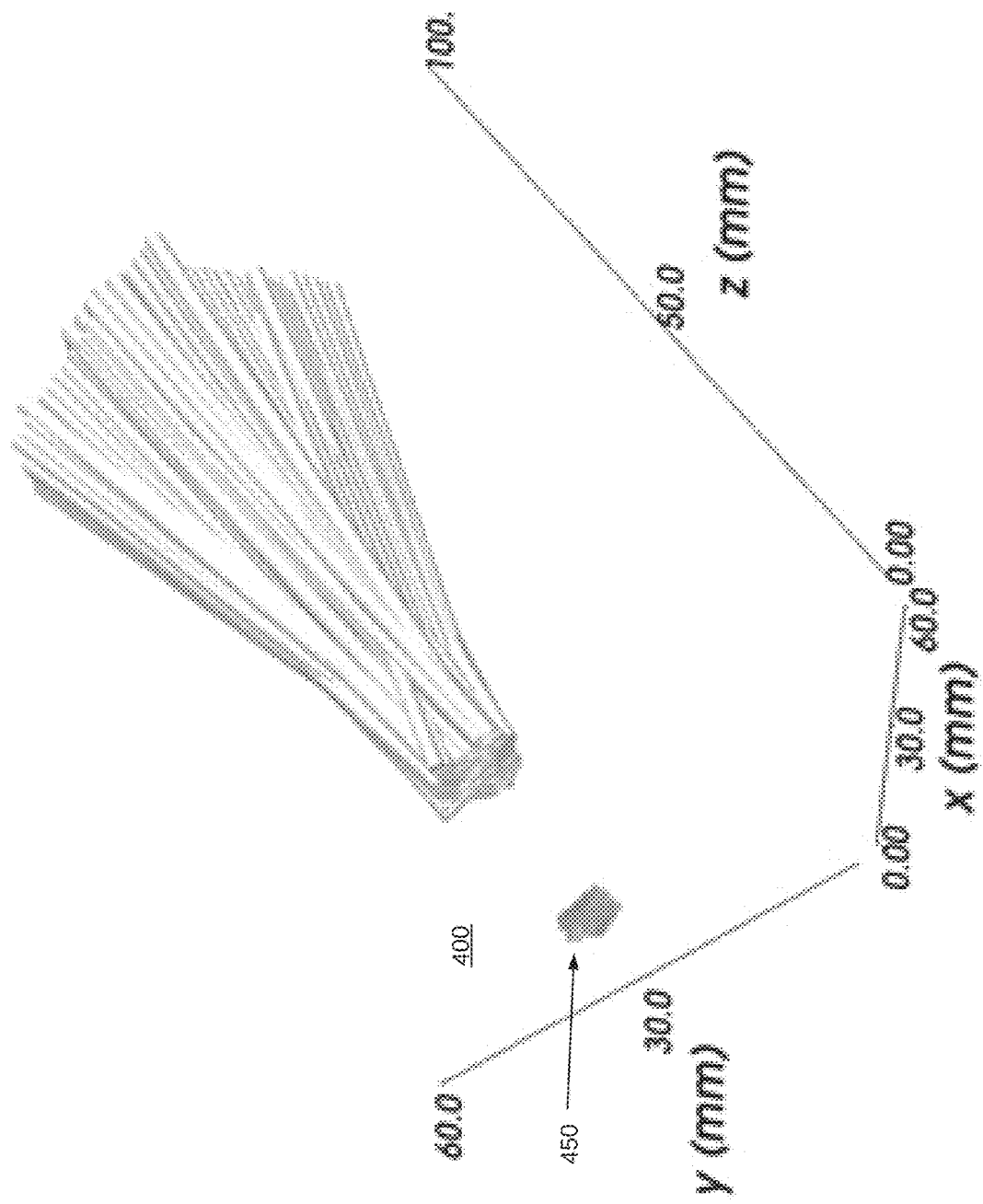
FIG. 4B is a three-dimensional diagram illustrating a plurality of ultrasound beams of insonation within the subject shown in FIG. 4A according to various arrangements.

FIG. 4B is a three-dimensional diagram illustrating a plurality of ultrasound beams of insonation within the subject shown in FIG. 4A according to various arrangements.

Referring to FIGS. 1-4B, FIG. 4B illustrates a perspective view of the subject's acoustic window and workspace 400 and the resulting ultrasound beams within the subject's head corresponding to the points of contact between the probe 105 and the subject at the workspace 400, as described with respect to FIG. 4A. As shown in FIG. 4B, each point of contact between the probe 105 and the subject is associated with a corresponding ultrasound beam of a given length that extends within the subject based on the orientation of the probe 105 at the point of contact. Accordingly, by moving the probe 105 at different locations along a subject and by orienting the probe 105 at different angles at a given point of contact or at different points of contact, ultrasound data can be acquired to accurately reconstruct a subject's vasculature insonated by the plurality of ultrasound beams.

Figure 5A:
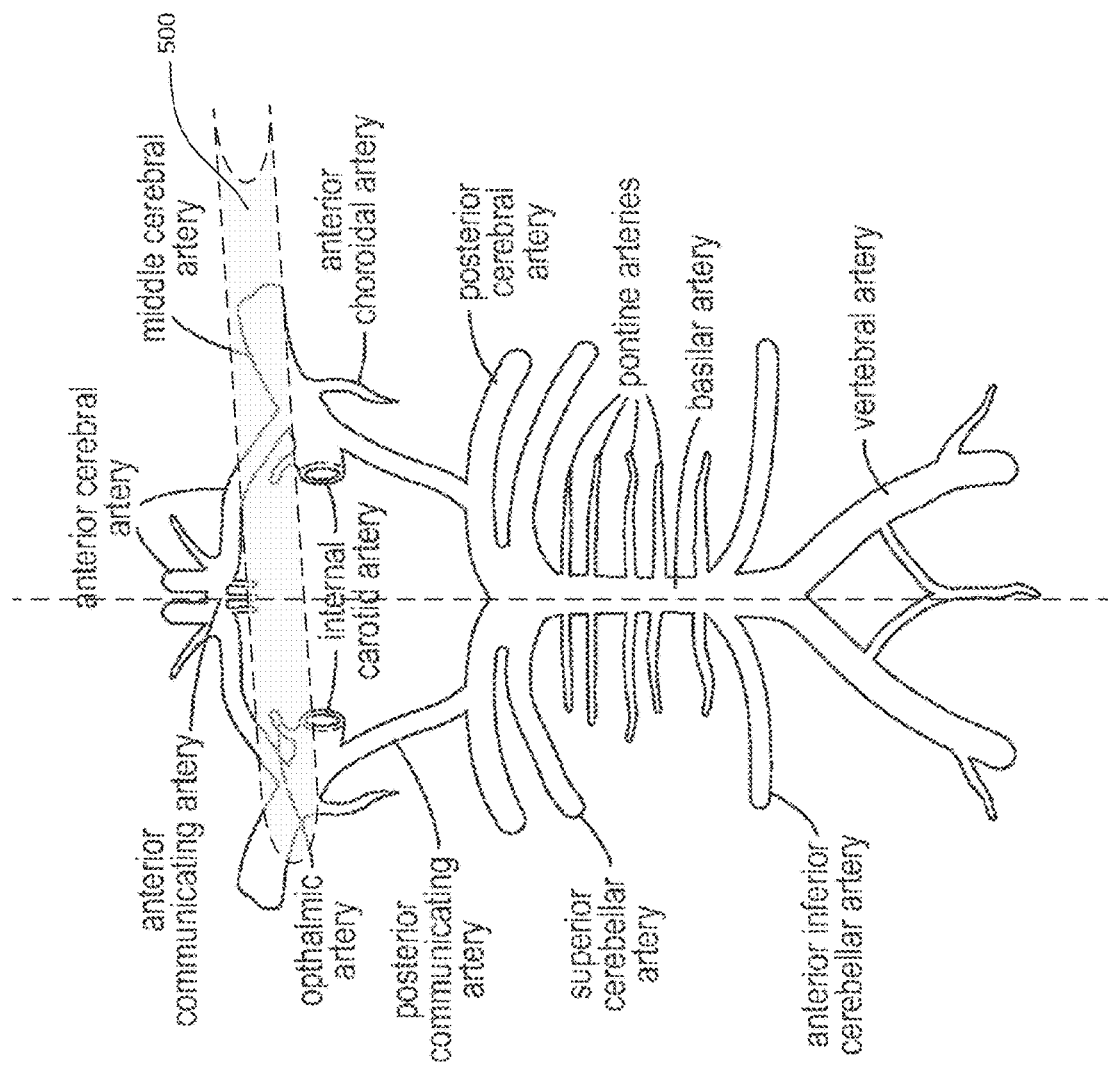
FIG. 5A is a diagram illustrating an ultrasound beam insonating a circle of Willis according to various arrangements.
Figure 5B:
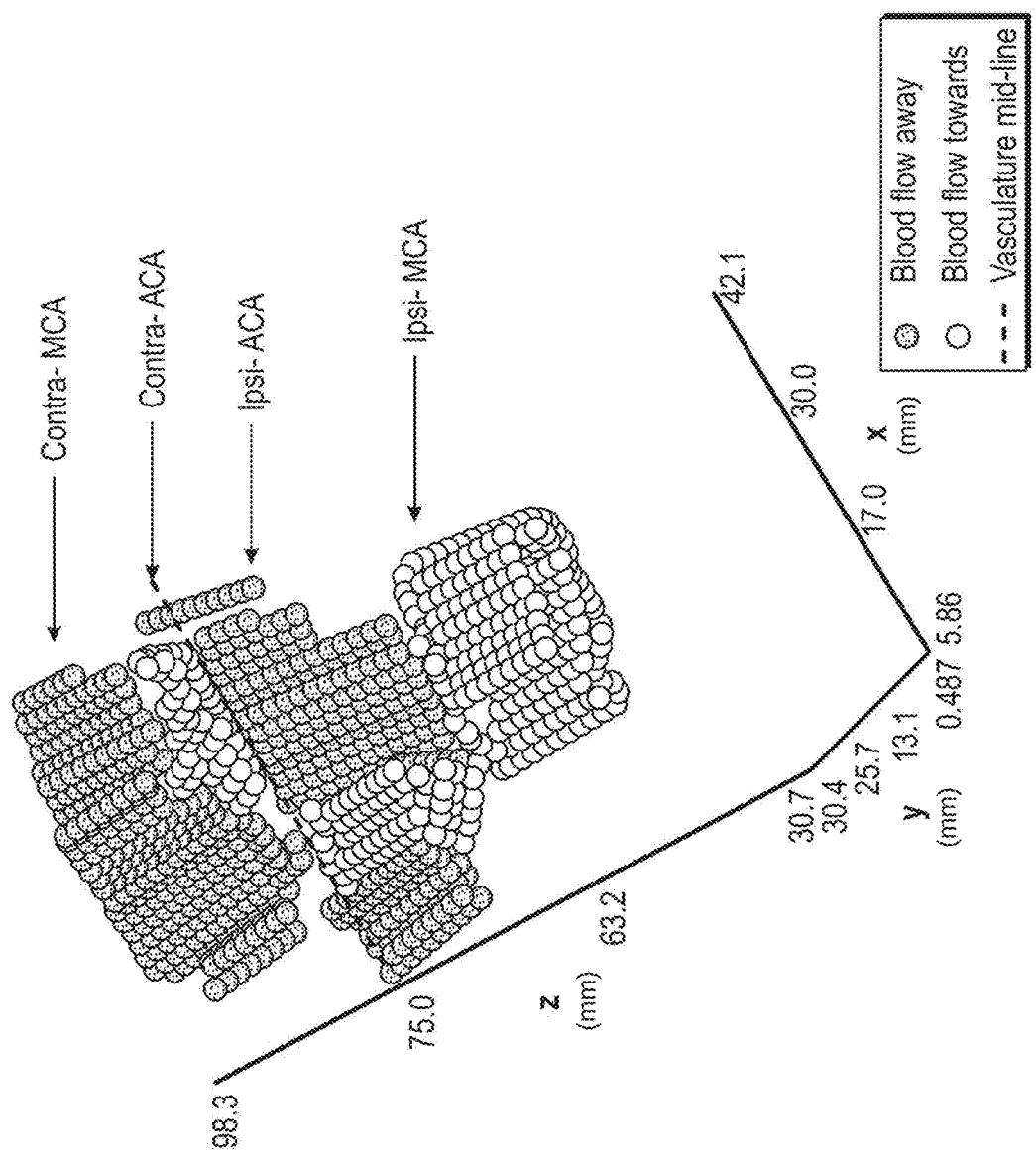
FIG. 5B is a three-dimensional diagram illustrating data collected by the ultrasound beam insonating the circle of Willis shown in FIG. 5A according to various arrangements.

FIG. 5A is a diagram illustrating an ultrasound beam 500 insonating a circle of Willis according to various arrangements. FIG. 5B is a three-dimensional diagram illustrating data collected by the ultrasound beam 500 insonating the circle of Willis shown in FIG. 5A according to various arrangements.

Referring to FIGS. 5A and 5B, the ultrasound beam 500 is shown to insonate multiple depths of the circle of Willis vasculature, for example, portions of the middle cerebral artery and anterior cerebral artery. As described above, the plurality of portions insonated by the ultrasound beam 500 can provide imaging parameters at those different portions, such as, but not limited to, presence of blood flow, direction of blood flow, and intensity or magnitude of the blood flow. As shown in FIG. 5B, the same ultrasound beam can reflect this ultrasound data at the insonated portions of the vasculature in three-dimensional space. Accordingly, this information can then be used to construct the vasculature map as described herein.

The above used terms, including "held fast," "mount," "attached," "coupled," "affixed," "connected," "secured," and the like are used interchangeably. In addition, while certain arrangements have been described to include a first element as being "coupled" (or "attached," "connected," "fastened," etc.) to a second element, the first element may be directly coupled to the second element or may be indirectly coupled to the second element via a third element.

The previous description is provided to enable any person skilled in the art to practice the various aspects described herein. Various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the term "some" refers to one or more. All structural and functional equivalents to the elements of the various aspects described throughout the previous description that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed as a means plus function unless the element is expressly recited using the phrase "means for."

It is understood that the specific order or hierarchy of steps in the processes disclosed is an example of illustrative approaches. Based upon design preferences, it is understood that the specific order or hierarchy of steps in the processes may be rearranged while remaining within the scope of the previous description. The accompanying method claims present elements of the various steps in a sample order, and are not meant to be limited to the specific order or hierarchy presented.

The previous description of the disclosed implementations is provided to enable any person skilled in the art to make or use the disclosed subject matter. Various modifications to these implementations will be readily apparent to those skilled in the art, and the generic principles defined herein may be applied to other implementations without departing from the spirit or scope of the previous description. Thus, the previous description is not intended to be limited to the implementations shown herein but is to be accorded the widest scope consistent with the principles and novel features disclosed herein.

The various examples illustrated and described are provided merely as examples to illustrate various features of the claims. However, features shown and described with respect to any given example are not necessarily limited to the associated example and may be used or combined with other examples that are shown and described. Further, the claims are not intended to be limited by any one example.

The foregoing method descriptions and the process flow diagrams are provided merely as illustrative examples and are not intended to require or imply that the steps of various examples must be performed in the order presented. As will be appreciated by one of skill in the art the order of steps in the foregoing examples may be performed in any order. Words such as "thereafter," "then," "next," etc. are not intended to limit the order of the steps; these words are simply used to guide the reader through the description of the methods. Further, any reference to claim elements in the singular, for example, using the articles "a," "an" or "the" is not to be construed as limiting the element to the singular.

The various illustrative logical blocks, modules, circuits, and algorithm steps described in connection with the examples disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

The preceding description of the disclosed examples is provided to enable any person skilled in the art to make or use the present disclosure. Various modifications to these examples will be readily apparent to those skilled in the art, and the generic principles defined herein may be applied to some examples without departing from the spirit or scope of the disclosure. Thus, the present disclosure is not intended to be limited to the examples shown herein but is to be accorded the widest scope consistent with the following claims and the principles and novel features disclosed herein.

It should be noted that although the diagrams herein may show a specific order and composition of method blocks, it is understood that the order of these blocks may differ from what is depicted. For example, two or more blocks may be performed concurrently or with partial concurrence. Also, some method blocks that are performed as discrete blocks may be combined, blocks being performed as a combined block may be separated into discrete blocks, the sequence of certain processes may be reversed or otherwise varied, and the nature or number of discrete processes may be altered or varied. The order or sequence of any element or apparatus may be varied or substituted according to alternative arrangements. Accordingly, all such modifications are intended to be included within the scope of the present disclosure as defined in the appended claims. Such variations will depend on the machine-readable media and hardware systems chosen and on designer choice. It is understood that all such variations are within the scope of the disclosure. Likewise, software and web arrangements of the present disclosure could be accomplished with standard programming techniques with rule based logic and other logic to accomplish the various database searching blocks, correlation blocks, comparison blocks, and decision blocks.

What is claimed is:

1. A method, comprising:
   receiving first ultrasound data including at least one imaging parameter of a first portion of a vasculature of a subject based on a first ultrasound beam, wherein the first ultrasound beam is transmitted by a probe at a first position relative to a body of the subject;
   receiving second ultrasound data including the at least one imaging parameter of a second portion of the vasculature based on a second ultrasound beam, wherein the first ultrasound beam is transmitted by the probe at a second position relative to the body of the subject;
   determining that ultrasound data acquired is enough for constructing a map of the vasculature, wherein the ultrasound data comprises the first ultrasound data and the second ultrasound data; and
   in response to determining that the ultrasound data acquired is enough for constructing the map, constructing the map of the vasculature based at least in part on the first position, the second position, the first ultrasound data, and the second ultrasound data.

2. The method of claim 1, further comprising
   moving the probe, by a robot connected to the probe, to the first position relative to the body; and
   transmitting, by the probe, the first ultrasound beam into the first portion of the vasculature.

3. The method of claim 2, wherein the first ultrasound beam simultaneously insonates a first plurality of depths.

4. The method of claim 1, further comprising
   moving the probe, by a robot connected to the probe, to the second position relative to the body; and
   transmitting, by the probe, the second ultrasound beam into the second portion of the vasculature.

5. The method of claim 4, wherein the second ultrasound beam simultaneously insonates a second plurality of depths.

6. The method of claim 1, the at least one imaging parameter comprises presence and vector direction of blood flow.

7. The method of claim 1, wherein determining that the ultrasound data acquired is enough for constructing the map comprises determining a number of ultrasound insonation.

8. The method of claim 1, wherein determining that the ultrasound data acquired is enough for constructing the map comprises determining an amount of ultrasound data.

9. The method of claim 1, wherein determining that the ultrasound data acquired is enough for constructing the map comprises determining a number of movements of the probe, wherein the movements comprise moving the probe to the first position relative to the body and moving the probe to the second position relative to the body.

10. The method of claim 1, wherein determining that the ultrasound data acquired is enough for constructing the map comprises determining an amount of time lapsed.

11. A non-transitory computer-readable medium having computer-readable instructions such that, when executed by a processor, configures the processor to:
   receive first ultrasound data including at least one imaging parameter of a first portion of a vasculature of a subject based on a first ultrasound beam, wherein the first ultrasound beam is transmitted by a probe at a first position relative to a body of the subject;
   receive second ultrasound data including the at least one imaging parameter of a second portion of the vasculature based on a second ultrasound beam, wherein the first ultrasound beam is transmitted by the probe at a second position relative to the body of the subject;

determine that ultrasound data acquired is enough for constructing a map of the vasculature, wherein the ultrasound data comprises the first ultrasound data and the second ultrasound data; and in response to determining that the ultrasound data acquired is enough for constructing the map, construct the map of the vasculature based at least in part on the first position, the second position, the first ultrasound data, and the second ultrasound data.

12. The non-transitory computer-readable medium of claim 11, the at least one imaging parameter comprises presence and vector direction of blood flow.

13. The non-transitory computer-readable medium of claim 11, wherein determining that the ultrasound data acquired is enough for constructing the map comprises determining a number of ultrasound insonation.

14. The non-transitory computer-readable medium of claim 11, wherein determining that the ultrasound data acquired is enough for constructing the map comprises determining an amount of ultrasound data.

15. The non-transitory computer-readable medium of claim 11, wherein determining that the ultrasound data acquired is enough for constructing the map comprises determining a number of movements of the probe, wherein the movements comprise moving the probe to the first position relative to the body and moving the probe to the second position relative to the body.

16. The non-transitory computer-readable medium of claim 11, wherein determining that the ultrasound data acquired is enough for constructing the map comprises determining an amount of time lapsed.

17. A tool, comprising:
at least one processing circuit configured to:
receive first ultrasound data including at least one imaging parameter of a first portion of a vasculature of a subject based on a first ultrasound beam, wherein the first ultrasound beam is transmitted by a probe at a first position relative to a body of the subject;

receive second ultrasound data including the at least one imaging parameter of a second portion of the vasculature based on a second ultrasound beam, wherein the first ultrasound beam is transmitted by the probe at a second position relative to the body of the subject;

determine that ultrasound data acquired is enough for constructing a map of the vasculature, wherein the ultrasound data comprises the first ultrasound data and the second ultrasound data; and in response to determining that the ultrasound data acquired is enough for constructing the map, construct the map of the vasculature based at least in part on the first position, the second position, the first ultrasound data, and the second ultrasound data.

18. The tool of claim 17, further comprising a probe, wherein the probe is moved to the first position relative to the body to transmit the first ultrasound beam into the first portion of the vasculature; and the probe is moved to the second position relative to the body to transmit the second ultrasound beam into the second portion of the vasculature.

* * * * *